United States Patent [19]

Cuatrecasas et al.

[11] 4,125,492

[45] Nov. 14, 1978

[54] AFFINITY CHROMATOGRAPHY OF VIBRIO CHOLERAE ENTEROTOXIN-GANGLIOSIDE POLYSACCHARIDE AND THE BIOLOGICAL EFFECTS OF GANGLIOSIDE-CONTAINING SOLUBLE POLYMERS

[76] Inventors: Pedro Cuatrecasas, 10 Hillside Rd.; Indu Parikh, 4404 Keswick Rd., both of Baltimore, Md. 21210

[21] Appl. No.: 713,095

[22] Filed: Aug. 10, 1976

Related U.S. Application Data

[63] Continuation of Ser. No. 475,313, May 31, 1974, abandoned.

[51] Int. Cl.$^2$ ............................ C08L 1/02; C08L 3/02; C08L 5/02
[52] U.S. Cl. ..................................... 260/9; 210/31 C; 260/112 R; 536/4; 424/12; 424/92
[58] Field of Search .................. 210/31 C; 195/63, 68, 195/DIG. 11; 260/9, 112 R, 209 R, 209 D, 121, 122, 212; 424/12, 92

[56] References Cited

U.S. PATENT DOCUMENTS 3,278,392  10/1966  Patchornik ........................... 195/63

OTHER PUBLICATIONS

Chem. Absts. vol. 79:102204t, "Isolation and Purification," Avrova.
Chem. Absts. vol. 79:75505h, "Stable — Chromatography," Wilchek.
Chem. Absts. vol. 75:72237d, "Purification — G-100," Faryna de Raveglia.
Chem. Absts. vol. 77:111023u, "Selective — Specificity," Cuatrecasas.
Science, vol. 179, pp. 1142-1144, "Biological — Sepharose," Cuatrecasas.

Primary Examiner—Edward M. Woodberry
Attorney, Agent, or Firm—Bacon & Thomas

[57] ABSTRACT

Columns of polysaccharide, e.g., agarose, derivatives comprising covalently bonded gangliosides quantitatively adsorb the $^{125}$I-labeled cholera toxin of chromatographed samples. The most preferred derivatives are those wherein the gangliosides are coupled to "macromolecules" [native albumin, denatured albumin, poly(L-lysine) and poly(L-lysyl-DL-alanine) graft copolymers] which themselves are covalently bonded to the, e.g., agarose. The soluble ganglioside polymers can prevent the binding of $^{125}$I-labeled toxin to liver membranes as well as block completely the lipolytic activity of cholera toxin on fat cells, and thus are useful in the management of the manifestations of clinical cholera.

15 Claims, No Drawings

AFFINITY CHROMATOGRAPHY OF VIBRIO CHOLERAE ENTEROTOXIN-GANGLIOSIDE POLYSACCHARIDE AND THE BIOLOGICAL EFFECTS OF GANGLIOSIDE-CONTAINING SOLUBLE POLYMERS

This is a continuation, of application Ser. No. 475,313, filed May 31, 1974, now abandoned.

BACKGROUND OF THE INVENTION

1. Field of the Invention

The present invention relates to the preparation and use of certain insoluble polysaccharide derivatives comprising covalently linked gangliosides, and, more especially, relates to the use of such derivatives for the extraction and purification of cholera toxin by affinity chromatography techniques.

2. Cross Reference to Related Applications

1. Serial No. 475,305, filed May 31, 1974, now U.S. Pat. No. 3,947,352; hereby expressly incorporated by reference and relied upon.

2. Serial No. 475,314, filed May 31, 1974, now abandoned, and copending continuing application, Ser. No. 713,108, filed Aug. 10, 1976; hereby expressly incorporated by reference and relied upon.

3. Description of the Prior Art

It has recently been demonstrated that the enterotoxin from *Vibrio cholerae*, which is responsible for the gastrointestinal manifestations of clincial cholera, binds very strongly to gangliosides and less strongly to certain glycoproteins such as fetuin and thyroglobulin. Cuatrecasas, *Biochemistry*, 12, 3547 (1973a); Cuatrecasas, *Biochemistry*, 12, 3558 (1973b). Gangliosides block the biological effects of cholera toxin on isolated fat cells [Cuatrecasas, 1973a, supra; Cuatrecasas, 1973b, supra; van Heyningen et al, *J. Infec. Dis.*, 124, 415 (1971)] and on the small intestine [van Heyningen et al, supra; Pierce, *J. Exp. Med.*, 137, 1009 (1973); Holmgren et al, *Scand. J. Infec. Dis.*, 5, 77 (1973)], and they prevent the binding of $^{125}$I-labeled cholera toxin to specific receptors on the cell membranes of various tissues, such as adipose tissue, liver erythrocytes, and intestinal epithelial cells; Cuatrecasas, 1973a, b, supra. There is considerable evidence indicating that gangliosides, and specifically $G_{M1}$ gangliosides, are the natural membrane receptors with which cholera toxin specifically interacts to elicit its biological effects in tissues; Cuatrecasas, 1973a, b, supra.

SUMMARY OF THE INVENTION

It has now been determined according to the invention that certain insoluble polysaccharide, e.g., agarose, derivatives comprising covalently linked gangliosides are useful for the extraction and purification of cholera toxin by affinity chromatography [Cuatrecasas et al, *Proc. Nat. Acad. Sci. U.S.*, 61, 636 (1968); Cuatrecasas, *Advan. Enzymol.*, 35, 29 (1972a); Cuatrecasas, *Proc. Nat. Acad. Sci. U.S.*, 69, 1277 (1972b)]. The utility of such insoluble biospecific adsorbents, as well as of soluble polymers which contain covalently coupled gangliosides, in the therapeutic approach to clinical cholera is demonstrated by evidencing that such derivatives effectively block the binding and the metabolic effects of cholera toxin in isolated adipocytes.

Briefly, according to the invention, columns of agarose derivatives [other polysaccharide derivatives include cellulose, starch, and the cross-linked polysaccharide gels, Sephadex and Sepharose] containing covalently attached gangliosides quantitatively adsorb the $^{125}$I-labeled cholera toxin of chromatographed samples. The most effective derivatives are those in which the gangliosides are coupled to "macromolecules" [native albumin, denatured albumin, poly-L-lysine and poly(L-lysyl-DL-alanine) graft copolymers] which are covalently linked to agarose. Ganglioside adsorbents [1-ml columns] comprising such macromolecular "arms" can effectively adsorb cholera toxin even after the adsorbent is diluted 200- to 600-fold with unsubstituted agarose. Compare application, Serial No. 475,314, now abandoned, and copending continuation application, Ser. No. 713,108, supra. Selective adsorption is blocked if the toxin is incubated with free gangliosides before chromatography. Quantitative elution is achieved with buffers containing 5-7 M guanidine.HCl. The biological activity of purified samples of cholera toxin is completely removed by chromatography on small ganglioside-agarose affinity columns, and this activity can be quantitatively recovered upon elution with guanidine.HCl. Small [5-ml] affinity columns can remove virtually all [more than 99%] of the cholera toxin activity and $^{125}$I-labeled toxin present as a tracer in preparations of filtrates of Vibrio cholerae derived from about 41. of crude culture medium. Ganglioside-agarose beads can block the lipolytic effects of cholera toxin on isolated fat cells. Soluble ganglioside polymers, prepared by covalently attaching the glycolipids to branched copolymers of lysine and alanine (see again application, Serial No. 475,314, now abandoned, and copending continuation application, Ser. No. 713,108, supra), can prevent the binding of $^{125}$I-labeled toxin to liver membranes, as well as block completely the lipolytic activity of cholera toxin on fat cells. These polymeric ganglioside derivatives thus are useful in the management of the manifestations of clinical cholera. Studies with sodium dodecyl sulfate disc gel electrophoresis indicate, albeit applicant does not wish to be bound by this theory, that cholera toxin is composed of two major subunits having molecular weights of about 66,000 and 36,000. Reduction and alkylation convert the larger subunit into components having a molecular weight of about 8,000, and the smaller subunit is converted to two components having molecular weights of about 27,000 and 8,000; the mole of disulfide bonds in maintaining or stabilizing the oligomeric structure of the two major subunits is uncertain. The larger subunit [molecular weight 66,000] appears to be very similar to or identical with choleragenoid, a toxin derivative which is antigenically very similar to toxin, which is biologically inactive, and which competitively inhibits the binding and biological activity of cholera toxin. The smaller subunit [molecular weight 36,000] does not appear to bind to cells. Hence, it is proposed that the ability of cholera toxin to bind specifically to cells is governed solely by the larger subunit, but that the ability to elicit a specific biological response resides in the smaller subunit. Cholera toxin is thus suggested to consist of one subunit which acts to deliver to the cell membrane, in a highly specific manner, another molecule [subunit] which in turn is capable of inducing subsequent changes which lead to the biological response.

DETAILED DESCRIPTION OF THE INVENTION

General Properties of Affinity Adsorbents. Whereas [$^{125}$I]-cholera toxin does not bind to columns containing unsubstituted agarose, a substantial portion of the radioactivity does adsorb to columns containing fetuin-agarose or A-DADA-gang[1]; compare FIG. 1, Table I and the methodology appurtenant thereto, Cuatrecasas et al, *Biochemistry*, 12, No. 21, 4253 at page 4255 (1973e), hereby expressly incorporated by reference and relied upon. About 80% of the radioactivity in the iodinated toxin preparation can bind specifically to liver membranes before chromatography. About 30% of the radioactive material applied to a fetuin-agarose column is not adsorbed, and about 20% of this material can still bind selectively to liver membranes. The ganglioside-agarose adsorbent appears to be more effective than that which contains fetuin since 15-20% of the radioactive material which is applied to the column appears in the breakthrough of the column, and virtually none of this material can bind selectively to liver membranes. It appears that about 15-20% of the total radioactive content of [$^{125}$I]cholera toxin represents radioactivity on denatured or contaminating protein. The specificity of the adsorptive process is further illustrated by demonstrating that incubation of the [$^{125}$I]cholera toxin with gangliosides before chromatography effectively prevents the subsequent adsorption of radioactivity to the column.

[1] ganglioside-diaminodipropylamine-agarose

In the experiments described in said FIG. 1, Cuatrecasas et al, 1973e, *supra*, elution of the adsorbed [$^{125}$I]-toxin was achieved with 7 M guanidine.HCl. Experiments were performed to determine whether milder conditions could be utilized to elute the toxin from such columns. The strength with which the toxin is adsorbed is evident from the inability to achieve elution with 0.1 M acetic acid, 2 N NaCl, and 3 M guanidine.HCl containing 1 N NaCl. Even 4 M guanidine.HCl results in the elution of only about one-third of the bound toxin. Nearly quantitative elution, however, can be obtained with higher concentrations (5 M) of guanidine.HCl or with 0.1 N HCl.

Samples which had been chromatographed on A-DADA-gang columns such as that described in the aforesaid Cuatrecasas et al, 1973e, FIG. 1 contained detectable amounts of free gangliosides. Because the presence of this compound in the samples can interfere with assays of the breakthrough materials, and it can also potentially interfere with adsorption of the toxin to the column, experiments were performed to determine if other derivatives were less susceptible to this "leakage" phenomenon [Table II, Cuatrecasas et al, 1973e, supra, at page 4256]. Since the presence of free gangliosides in the column breakthrough samples is meaningful only when considered in relation to the concentration and effectiveness of the selective adsorbent, the various derivatives were diluted serially with unsubstituted agarose and their ability to extract [$^{125}$I]cholera toxin was compared. As predicted from the considerations described earlier, it is clear that the leakage of free gangliosides from the adsorbents which contain macromolecular spacers [native albumin, denatured albumin, poly-L-lysine and poly(-L-lysyl-DL-alanine) graft copolymer] is much less marked than that which occurs with A-DADA-gang. Of equal importance, however, is the fact that the adsorbents containing the polymeric spacers are inherently much more effective in extracting the toxin. It is notable that these derivatives are quite effective even when diluted 50-fold with unsubstituted agarose. The most preferred derivative appears to be A-NatAlb-gang[2]; with this adsorbent some adsorption is detectable even after a 600-fold dilution. Furthermore, leakage is not a problem in this case since no significant free ganglioside is detectable in effluents of columns containing a 10-fold diluted adsorbent. Experiments of this type, which are quite useful in comparing the relative effectiveness of a variety of adsorbents, indicate that fetuin-agarose is quite inferior to any of the ganglioside-agarose derivatives since virtually no adsorption occurs to adsorbents diluted 1:10 with unsubstituted agarose.

[2] ganglioside-native albumin-agarose

The chromatographic behavior of a sample of purified cholera toxin containing a tracer quantity of [$^{125}$I]-toxin on a column containing A-Alb-gang is presented in FIG. 2 and Table III of said Cuatrecasas et al, 1973e, *supra*, at page 4257. Adsorption is prevented by incubating the toxin with gangliosides before chromatography. In the absence of gangliosides the column extracts 70% of the protein and more than 95% of the lipolytic activity. The protein which does not adsorb to the column is virtually without lipolytic activity and the radioactivity in this peak does not bind to liver membranes. Nearly 90% of the lipolytic activity applied to the column is recovered upon elution with 7 M guanidine.HCl. These experiments demonstrate that the behavior of $^{125}$I-labeled and native cholera toxin on such affinity columns is very similar.

Chromatography of Crude Vibrio cholerae Filtrates on Affinity Columns. The total material obtained from 3.4 l. of crude culture medium of *V. cholerae* was chromatographed on a 5-ml column of A-NatAlb-gang (FIG. 3 and Table IV of said Cuatrecasas et al, 1973e, *supra*, at pages 4257-4258). More than 99% of the lipolytic activity and 80% [or virutally all of the active form] of the tracer $^{125}$I-labeled toxin present in this material disappeared after passage through this column, and no free gangliosides could be detected in the effluent samples. After very thorough and prolonged washing, elution with 5 M guanidine.HCl resulted in the recovery of about 1 mg of protein and at least 70% of the $^{125}$I-labeled toxin which had adsorbed to the column. On the basis of radioactivity, the toxin was purified more than 90-fold by this procedure.

The material eluted from this column was virtually devoid of biological activity. The lack of activity in this material is not explained by the presence of gangliosides or of residual guanidine [which inhibits lipolysis] since it did not alter the lipolytic response of native cholera toxin when these were incubated together before assay. The lack of activity is similarly not explained by the presence of biologically inactive choleragenoid, which can block the binding and activity of cholera toxin [Cuatrecasas, *Biochemistry*, 12, 3577 (1973d)], since preincubation of cells with the eluted material did not block the binding of $^{125}$I-labeled toxin or the lipolytic response to native toxin. Data presented suggests that the loss of activity may have resulted from dissociation of the toxin into subunits, as aforesaid; this process is essentially irreversible when the concentration of cholera toxin is very low. In some experiments it has been possible to elute about 10-20% of the lipolytic activity adsorbed, although the reasons for such recovery in certain experiments is not known.

In the experiment described in the noted Cuatrecasas et al, 1973e, FIG. 3, *supra*, it was estimated on the basis of lipolytic activity that the entire material applied to the column contained about 3.5 mg of cholera toxin. Since all of the activity and all of the active radioactivity were removed by the column, and since the recovery of adsorbed radioactivity upon elution was about 70%, it was anticipated that elution should have yielded about 2.4 mg of protein had the purification been complete. However, only 1.3 mg of protein was present in the eluted sample. The reason for the slight but significant disparity between the quantity of protein actually eluted and that anticipated is not apparent. It is possible that alterations of the native toxin, not reflected in the $^{125}$I-labeled material, occur during the step of concentration of the crude toxin since this exposes the protein to high ionic strength.

Since in the experiment depicted all of the cholera toxin applied on the column was extracted from the sample, the binding capacity of such columns was examined. When the quantity of sample applied was increased by 2.5 times and the adsorbent was diluted 5-fold with unsubstituted agarose, only one-third of the cholera toxin applied was adsorbed to the column [FIG. 4, Cuatrecasas et al, 1973e, *supra*, at page 4259]. The toxin was effectively extracted from the first effluent fractions while virtually no extraction occurred in the last fractions. As in the other experiments, only a very small proportion of the total protein was adsorbed to the column, and elution of the radioactively labeled toxin was satisfactory. There was excellent correspondence between the appearance of radioactivity and lipolytic activity in the breakthrough fractions, pointing again to the similarity in the behavior of the labeled and native toxins. The use of $^{125}$I-labeled tracers in these experiments greatly facilitates monitoring and quantitation of the chromatographic experiments.

Reversible Denaturation of Cholera Toxin. The binding of cholera toxin to the affinity columns is so strong that to achieve elution it is necessary to use buffers which are likely to unfold, and possibly denature, the protein. Because of this, and because the protein eluted from columns on which crude samples were chromatographed yielded essentially inactive toxin preparations, the ability of cholera toxin to renature after removal of denaturants was examined [Table V, Cuatrecasas et al, 1973e, supra, at page 4259]. Brief exposure of [$^{125}$I]cholera toxin to acidic and basic conditions, and to relatively low concentrations of urea and guanidine.HCl, diminishes profoundly the ability of the iodoprotein to bind to liver membranes upon dilution or neutralization of the denaturant; similar effects are observed if urea and guanidine.HCl are removed by dialysis. The $^{125}$I-labeled toxin which is eluted from affinity columns such as those depicted in the aforesaid noted FIG. 1 and Tables I and II does not bind at all to liver membranes if tested after removal of guanidine.HCl. These results suggest that the $^{125}$I-labeled toxin is undergoing an irreversible unfolding or denaturation. The conditions which cause this irreversible effect occur with concentrations of urea and guanidine.HCl which are lower than those which are required to elute the toxin which is adsorbed to a ganglioside-agarose column. This suggests that ganglioside binding greatly stabilizes the tertiary or quaternary structure of the protein.

The effects described immediately above suggest results contradictory to those of the experiments described in the noted FIG. 2, where guanidine.HCl elution of a chromatographed sample of purified toxin yielded active toxin. The possibility was examined that the irreversible denaturation described is dependent on the concentration of toxin used in such experiments. Samples of native cholera toxin [0.1–0.5 mg/ml] containing a tracer of $^{125}$I-labeled toxin were exposed for 25 min. at 24° to (a) 0.1 M phosphate buffer [pH 7.4], (b) distilled water, (c) 0.1 N HCl, (d) 7 M guanidine.HCl, and (e) 7 M urea under conditions similar to those described in the Cuatrecasas et al, 1973e, Table V. The samples were then diluted fivefold and dialyzed overnight against large volumes of Krebs-Ringer-bicarbonate buffer. Virtually no radioactivity was lost during the period of dialysis, and the lipolytic activity of all the samples was equal to that of the sample exposed only to phosphate buffer. It is clear that at these concentrations of cholera toxin, which are about 10,000 times higher than those described in said Table V, denaturation of the toxin by exposure of these solvents is readily reversible.

There is some evidence that the denaturation described above involves a process of dissociation of cholera toxin into subunits. As suggested above, exposure of high concentrations [0.5 mg/ml] of toxin to 7 M guanidine.HCl followed by dialysis does not result in the loss of the $^{125}$I-labeled toxin which is added as a tracer. In contrast, exposure of tracer quantities [10 ng/ml] of $^{125}$I-labeled toxin to 7 M guanidine.HCl results in the rapid loss of radioactivity upon dialysis, even when 0.1% albumin is added to the sample to prevent adsorption to the dialysis membrane. Under these conditions 60% of the radioactivity is lost after dialysis for 2 hours at 24°, and about 85% is lost after dialysis for 24 hours at 4°. Further evidence for the dissociation into subunits comes from disc gel electrophoretic experiments in 0.5% sodium dodecyl sulfate, Cuatrecasas et al, 1973e, supra, at pages 4260–4262. These results are consistent with findings of LoSpalluto and Finkelstein, *Biochim. Biophys. Acta*, 257, 158 (1972), who described reversible dissociation of cholera toxin into subunits of about 15,000 molecular weight upon exposure to 6 M urea or to a pH 3.6; these experiments were performed at concentrations of toxin varying from 2.5 to 4 mg per ml.

Ganglioside-Agarose and the Lipolytic Response to Cholera Toxin. The ganglioside-agarose derivatives described herein are quite effective in removing $^{125}$I-labeled toxin from buffer solutions when the derivatized beads are added and incubated in suspension. The derivatives can be diluted with unsubstituted agarose, and adsorption is generally complete after incubating for 15 min. at 24°. The derivatives are also quite potent in protecting fat cells against the metabolic effects of the toxin provided that the beads are added to the cells before the toxin [Table VI, Cuatrecasas et al, 1973e, supra, at page 4260]. Addition of the adsorbent 10 min. after addition of the toxin has no effect on the lipolytic response to the toxin. These results are consistent with the nearly irreversible nature of the binding of cholera toxin to cell membranes [Cuatrecasas, 1973a, b, supra].

Effect of Water-soluble Polymers Containing Gangliosides. The water-soluble copolymer of poly(L-lysine) (backbone) and -(DL-alanine) (side branches) which contains covalently linked gangliosides effectively inhibits the binding of $^{125}$I-labeled cholera toxin to liver membranes [Table VII, Cuatrecasas et al, 1973e, supra, at page 4260]. This ganglioside polymer is effective in concentrations which in the final incubation medium are as low as 0.1 µg/ml.

The ganglioside-containing polymer is also quite effective in blocking the lipolytic effect of cholera toxin on fat cells [Table VIII, Cuatrecasas et al, 1973e, supra, at page 4260]. However, as with the insoluble ganglioside derivatives, marked effects are observed only if the polymer is added to the cells before the addition of cholera toxin. These soluble derivatives appear to be more potent than the comparable insoluble agarose derivatives. Nearly complete inhibition of activity is achieved with concentrations of the polymer as low as 0.5 μg/ml.

Disc gel electrophoretic characterization of cholera toxin and choleragenoid consistent with the invention too is described at Cuatrecasas et al, 1973e, supra, at pages 4260–4262. Experimental Materials. The crude culture filtrate cholera toxin from *Vibrio cholerae* was lot 002 [Wyeth], provided by the SEATO Cholera Research Program, NIAID. This material was prepared by lyophilization of culture filtrate of *V. cholerae* strain 569B, grown in Richardson's [Richardson and NoStle, *J. Infec. Dis.*, 121, Suppl. 73 (1970)] TRY medium; 100 g of this material represented the lyophilized filtrate of about 8.45 l. of crude culture medium. Cholera toxin [lot 1071], purified by the method of Finkelstein and LoSpalluto, *J. Infec. Dis.*, 121, Suppl., 563 (1970), was obtained from SEATO Cholera Research Program; it was prepared under contract for the National Institute of Allergy and Infectious Diseases by Dr. R. A. Finkelstein, The University of Texas Southwestern Medical School, Dallas, Texas. Choleragenoid was a gift from Dr. Finkelstein. Bovine brain gangliosides [grades II and III] were purchased from Sigma. Procine thyroglobulin was obtained from Miles, fetuin from Calbiochem, bovine albumin [grade A] from Pentex, guanidine.HCl [Ultra Pure] and urea from Schwarz-Mann, Sepharose 4B from Pharmacia, dicyclohexylcarbodiimide and 1-ethyl-3-(3-dimethylaminopropyl)carbodiimide from Pierce, and N-hydroxysuccinimide from Aldrich. The multichain copolymer, poly(L-lysyl-DL-alanine), which consists of a polylysyl backbone and has an alanine to lysine ratio of 15 to 1, was purchased from Miles; the molecular weight of this compound was about 37,500. Poly(L-lysine).HCl [mol wt 160,000] was obtained from Schwarz-Mann.

Procedures. [$^{125}$I]Cholera toxin [5–20 μCi/μg] was prepared from toxin samples chromatographed on Sephadex G-75 by procedures described at Cuatrecasas, 1973a, *supra*. About 80% of the radioactive material prepared in this way bound specifically to liver membranes. The molecular weight of cholera toxin was assumed to be 84,000 and the $A_{1}{}^{1\%}{}_{cm}$ [280 nm] 11.41 [LoSpalluto and Finkelstein, *supra*]. Isolated fat cells were prepared from male Sprague-Dawley rats [90–120 g] by the method of Rodbell, *J. Biol. Chem.*, 241, 140 (1966). Liver membranes were prepared by homogenization in 0.25 M sucrose followed by differential centrifugation [Cuatrecasas, 1972b, *supra*]. Protein content was determined by the method of Lowrey et al, *J. Biol. Chem.*, 193, 265 (1951) using bovine albumin as the standard.

The specific binding of [$^{125}$I] cholera toxin to liver membranes was performed as described previously [Cuatrecasas, 1973a, b, *supra*]. Liver membranes [20–100 μg of protein] were incubated for 20 min. at 24° in Krebs-Ringer-bicarbonate buffer [pH 7.4], containing 0.1% albumin and the iodinated toxin [5–10 × $10^4$ cpm]; binding was determined by filtration on cellulose acetate (EGWP, Millipore Corp.) filters. For every determination nonspecific binding was determined by including control samples in which native toxin [5 μg/ml] was added to the membranes before adding [$^{125}$I]toxin. The presence of free gangliosides in column effluents was determined by measuring the ability of these samples to block the binding of [$^{125}$I]cholera toxin to liver membranes [Cuatrecasas, 1973a, b, supra]. The iodoprotein was incubated with the sample for 50 min. at 24° in Krebs-Ringer-bicarbonate buffer [pH 7.4], containing 0.1% albumin before determining specific binding. By these methods it is possible to detect less than 50 ng/ml of crude bovine brain gangliosides [type III, Sigma].

Lipolysis by fat cells was studied by determining the concentration of glycerol in the medium by the method of Ryley, *Biochem. J.*, 59, 353 (1955). The bioassay of cholera toxin was based on the potent lipolytic action of the toxin on fat cells. Fat cells [2–8 × $10^5$ cells/ml] were incubated at 37° in Krebs-Ringer-bicarbonate buffer containing 3° albumin; samples [0.1 ml] were analyzed for glycerol at various time periods between 90 and 160 min. [Cuatrecasas, *Biochemistry*, 12, 3567 (1973c)]. Since the absolute lipolytic responses varied between experiments, the activity of unknown toxin samples were expressed on the basis of comparisons with standard curves obtained with native cholera toxin.

Protein was analyzed by electrophoresis in 7.5% polyacrylamide disc gels [7.5 × 0.5 cm] at pH 7.0 in 0.1 M sodium phosphate buffer, both in the presence and absence of sodium dodecyl sulfate [Weber and Osborn, *J. Biol. Chem.*, 244, 4406 (1969)]. Protein was detected by staining 1–2 hours with Coomassic Brilliant Blue [0.25% in methanol water-acetic acid (5:5:1, v/v)], and gels were destained overnight in water-acetic acid-methanol [35:3:2, v/v]. Molecular weights were estimated from electrophoretic mobilities of standard proteins [cytochrome c, ovalbumin, serum albumin] in gels containing 0.1% sodium dodecyl sulfate.

Preparation of Ganglioside-Agarose Derivatives. Poly(L-lysine) and the branched, multichain copolymer of L-lysine ("backbone") and DL-alanine ("side arms") were coupled to cyanogen bromide activated agarose by the methods of Sica et al, *Nature (London), New Biol.*, 244, 36 (1973a); Sica et al, *J. Biol. Chem.*, in press (1973b); Cuatrecasas, *J. Biol. Chem.*, 245, 3059 (1970); copending application, Ser. No. 475,305, now U.S. Pat. No. 3,947,352; and application, Ser. No. 475,314, and copending continuation applicaton, Ser. No. 713,108. These polymers were used to increase the number of potentially modifiable functional groups [α-amino groups in the copolymer, ε-amino groups on the homopolymer] on the agarose, to place these groups at a considerable distance from the agarose backbone, and to enhance the likelihood of multipoint attachment of the soluble polymer on the agarose, which would increase the stability of linkage of subsequently substituted ligands. The derivatives used contained about 1.2 mg of copolymer/ml of agarose and about 1.4 mg of poly(L-lysine)/ml of agarose. Albumin was also used as a macromolecular spacer for the same reasons described above. Albumin was coupled to cyanogen bromide activated agarose in the absence [native] or presence [denatured] of 10 M urea, as described recently [Sica et al, 1973a, b, *supra*]; these derivatives contain 2–3 mg of albumin/ml of gel. 3,3'-Diaminodiproplamine, fetuin, and thyroglobulin were coupled to agarose with cyanogen bromide [Cuatrecasas, 1970, *supra*]; these agarose derivatives contained about 10 μmol. 6 mg, and 8 mg, respectively, of the ligand and proteins per ml of packed gel.

Gangliosides were coupled through carboxy groups of the terminal sialic acid residues to amino groups of the derivatized agaroses by utilizing a water-soluble carbodiimide reagent or dicyclohexylcarbodiimide, by preparing an active N-hydroxysuccinimide ester of the ganglioside, or by preparing an activated, mixed anhydride of the ganglioside.

Coupling with Carbodiimides. Ther derivatized agarose [containing amino groups] [25 ml] was washed and suspended in 50 ml of 50% (v/v) aqueous dioxane. Brain gangliosides [type III, Sigma] [50 mg] were added and the suspension was gently shaken at 24° for 15 min. 1-Ethyl-3-(3-dimethylaminopropyl)carbodiimide [100 mg] was added and the suspension was shaken for 6 hours at 24°, and another 100 mg portion of the carbodiimide was added. After shaking for another 12 hours, the gel was washed with 500 ml of water, 500 ml of 75% (v/v) aqueous methanol, 250 ml of 6 M guanidine.HCl, and 500 ml of water. The content of ganglioside, as judged by the recovery of unreacted ganglioside, was about 0.5 mg/ml of gel. Coupling was also performed in an organic solvent by reacting 20 mg of ganglioside and 5 mg of dicyclohexylcarbodiimide in 10 ml of dioxane for 30 minutes at 15°. This was added to 20 ml of albumin-agarose suspended in dioxane in a total volume of 40 ml. After reacting for 15 hours at 24°, the gel was washed with 500 ml of dioxane, 500 ml of 90% (v/v) methanol, and 250 ml of 6 M guanidine. HCl.

N-Hydroxysuccinimide Ester. Ganglioside [20 mg] was reacted with 2.5 mg of N-hydroxysuccinimide and 2.5 mg of dicyclohexylcarbodiimde for 30 min. at 15° in 10 ml of dioxane. The solution was then added to 20 ml of albumin agarose suspended is dioxane [total volume, 40 ml]. After shaking for 15 hours at 24°, the gel washed as above described [water-soluble carbodiimide reaction].

Mixed Anhydride. A 100-μl portion of 0.1 M N-methylmorpholine in tetrahydrofuran was added to a solution of anhydrous tetrahydrofuran containing 20 mg of ganglioside. After stirring the solution for 10 min. at 0°, 100 l of 0.1 M isobutyl chloroformate [Vaughan and Osato, J. Amer. Chem. Soc., 74, 676 (1952)] in tetrahydrofuran was added and the reaction was allowed to continue for 20 min. at 0°. The reaction mixture was added to 20 ml of the amino agarose derivative suspended in dioxane [total volume, 40 ml]. After reacting for 15 hours at 24° the gel was washed as above described.

Although all of the methods above described resulted in effective adsorbents, the most preferred results were consistently obtained with derivatives prepared with the water-soluble carbodimide and with the mixed anhydride.

Preparation of Water-Soluble Polymers Containing Gangliosides. Gangliosides were coupled to the branched-chain copolymer of lysine and alanine with 1-ethyl-3-(3-dimethylaminopropyl)carbodiimide; 20 mg of poly(L-lysyl-DL-alanine) was dissolved in 7 ml of water and 5 ml of methanol and 40 mg of ganglioside [dissolved in 10 ml of 50% aqueous methanol] were added. The mixture was stirred at 24° for 15 min. and two 40 mg portions of 1-ethyl-3-(3-dimethylaminopropyl)carbodiimide were added at 6-hour intervals. After stirring for an additional 12 hours, the reaction mixture was dialyzed against 4 l. of $H_2O$ for 15 hours and lyophilized. The sample was ten chromatographed on a column [2.4 × 70 cm] of Sephadex G-75 equilibrated with 25% aqueous methanol containing 0.005 M HCl; the flow rate was 15 ml/hr, 4 ml fractions were collected and the elution was monitored by continuously recording the absorbance at 256 nm. The peak in the void volume was collected, lyophilized, and rechromatographed on a column [1.6 × 26 cm] of Sephadex G-100 equilibrated with 6 M guanidine.HCl [12 ml/hr, 4 ml/fraction]. The material present in the first peak was dialyzed against four changes of $H_2O$ (4 l.) for 24 hours and lyophilized. The yield was 22 mg.

Thus, the present invention demonstrates that columns containing ganglioside-agarose derivatives can selectively extract cholera toxin even when the toxin is present in concentrations as low as $10^{-11}$ M. The most preferred adsorbents are those which contain macromolecular spacers [i.e., poly(amino acid) polymers, albumin] interposed between the agarose backbone and the covalently attached ganglioside. Some of these derivatives are still effective after 600-fold dilution with unsubstituted agarose. Such macromolecular adsorbents have recently proved most useful in the purification of estrogen receptors from the uterus [Sica et al, 1973a, b, *supra*]. It has been possible to purify estrogen receptors about 100,000-fold in a single step by using 20-fold diluted poly(L-lysyl-DL-alanine)-agarose derivatives containing covalently attached estradiol.

Among the specific advantages of the derivatives having "macromolecular" spacers is a high degree of ligand substitution which permits the use of the adsorbent in diluted form, and this results in a decrease in the nonspecific protein adsorptive properties of the gel. Furthermore, the ligand is separated from the agarose backbone by large distances, which in the case of the branched amino acid copolymer may be as great as 150 Å. The high probability that the interposing macromolecule is anchored to the insoluble polymer by multiple points greatly increased the overall chemical stability of the attached ligand by stabilizing the basic cyanogen bromide attachment of the unit to the agarose. This enhanced stability may be quite important in very high-affinity systems such as the present one in which leakage of even small quantities of the ligand may seriously interfere with the specific adsorptive behavior of the proteins. These derivatives, particularly those prepared with albumin, may in addition present a more favorable microenvironment for the specific ligand-protein interaction. This appears to be the case with the estradiol-agarose derivatives [Sica et al, 1973b, *supra*].

The ability of gangliosides to bind extremely tightly to cholera toxin, and thus to prevent the binding and the biological effects of the toxin in various tissues [Cuatrecasas, 1973a, b, *supra*], evidenced that gangliosides are useful therapeutic agents for clincial cholera. However, the demonstration that free gangliosides may be incorporated spontaneously into cell membranes, and that this can ultimately result in increased binding of the toxin and in enchanced biological effects [Cuatrecasas, 1973b, *supra*], suggests that the in vivo use of such agents may be dangerous if not ineffective. For this reason the insoluble and soluble polymeric ganglioside derivatives described herein are more rational agents for the therapeutic value of gangliosides in clinical cholera.

While the invention has been shown and described and pointed out with reference to certain preferred embodiments thereof, those skilled in the art will appreciate that various changes, modifications, substitutions, and omissions can be made by those skilled in the art without department from the spirit of the invention. It is intended, therefore, that the invention be limited only by the scope of the claims which follow.

What is claimed is:

1. In a polysaccharide matrix useful as an adsorbent for affinity chromatography techniques, the improvement which comprises a ganglioside molecule covalently coupled to the backbone of said polysaccharide matrix.

2. The polysaccharide matrix as defined by claim 1, wherein a spacer moiety is interposed between the polysaccharide matrix and the coupled ganglioside.

3. The polysaccharide matrix as defined by claim 2, wherein the spacer moiety comprises a polyfunctional macromolecular spacer coupled to the backbone of said polysaccharide matrix in multipoint attachment, the said polyfunctional macromolecule being selected from the group consisting of (1) poly-L-lysine, and (2) the graft copolymer, poly(L-lysly-DL-alanine), and the said ganglioside being covalently coupled to said polyfunctional macromolecule.

4. The polysaccharide matrix as defined by claim 1, further comprising a cholera toxin adsorbed thereto.

5. The polysaccharide matrix as defined by claim 2, further comprising a cholera toxin adsorbed thereto.

6. The polysaccharide matrix as defined by claim 3, further comprising a cholera toxin adsorbed thereto.

7. The polysaccharide matrix as defined by claim 3, wherein the polyfunctional macromolecule is poly(L-lysyl-DL-alanine), a graft copolymer of poly-L-lysine (backbone) and poly-DL-alanine (side chains).

8. The polysaccharide matrix as defined by claim 7, wherein the poly(L-lysyl-DL-alanine) has an average molecular weight of about 37,500 and a lysine to alanine ratio of about 1:15.

9. The polysaccharide matrix as defined by claim 3, wherein the polyfunctional macromolecule is poly-L-lysine.

10. The polysaccharide matrix as defined by claim 9, wherein the poly-L-lysine has an average molecular weight of about 160,000.

11. The polysaccharide matrix as defined by claim 3, wherein the polysaccharide is selected from the group consisting of cellulose, starch, cross-linked dextran, and agarose.

12. The polysaccharide matrix as defined by claim 11, wherein the polysaccharide is agarose.

13. The polysaccharide matrix as defined by claim 3, wherein the said polysaccharide-polyfunctional macromolecular complex is diluted with an unsubstituted polysaccharide gel.

14. The polysaccharide matrix as defined by claim 13, wherein the said dilution is about 200- to 600-fold.

15. The polysaccharide matrix as defined by claim 3, wherein the ganglioside is bovine brain ganglioside.

* * * * *